(12) United States Patent
Shirai et al.

(10) Patent No.: US 8,435,742 B2
(45) Date of Patent: May 7, 2013

(54) METHOD AND KIT FOR DETECTION/QUANTIFICATION OF TARGET RNA

(75) Inventors: Mutsunori Shirai, Yamaguchi (JP);
Hajime Fukunaga, Yamaguchi (JP);
Kazuhiko Fujiwara, Tokyo (JP);
Kanehisa Yokoyama, Tokyo (JP);
Kentaro Fujimoto, Tokyo (JP)

(73) Assignee: Yamaguchi University, Yamaguchi (JP)

( * ) Notice: Subject to any disclaimer, the term of this patent is extended or adjusted under 35 U.S.C. 154(b) by 365 days.

(21) Appl. No.: 12/739,978

(22) PCT Filed: Nov. 4, 2008

(86) PCT No.: PCT/JP2008/003169
§ 371 (c)(1),
(2), (4) Date: Apr. 28, 2010

(87) PCT Pub. No.: WO2009/057330
PCT Pub. Date: May 7, 2009

(65) Prior Publication Data
US 2011/0053150 A1    Mar. 3, 2011

(30) Foreign Application Priority Data
Nov. 1, 2007 (JP) ................ 2007-285108

(51) Int. Cl.
*C12Q 1/68* (2006.01)
*C12P 19/34* (2006.01)
*C12N 9/00* (2006.01)
*C07H 21/04* (2006.01)

(52) U.S. Cl.
USPC ......... 435/6.12; 435/91.2; 435/183; 536/24.3

(58) Field of Classification Search .......... None
See application file for complete search history.

(56) References Cited

U.S. PATENT DOCUMENTS
2004/0023284 A1    2/2004    Browne

FOREIGN PATENT DOCUMENTS

| JP | 08-256797 | 10/1996 |
|---|---|---|
| JP | 2002-512688 | 4/2002 |
| JP | 2002-233385 | 8/2002 |
| JP | 2006-025791 | 2/2006 |
| JP | 2006-061155 | 3/2006 |
| WO | WO 91/01384 | 2/1991 |
| WO | WO 01/94634 | 12/2001 |
| WO | WO 03/057914 | 7/2003 |
| WO | WO 03/097794 | 11/2003 |
| WO | WO 2008/080029 | 7/2008 |

OTHER PUBLICATIONS

Fykse et al., "Detection of *Vibrio cholerae* by Real-Time Nucleic Acid Sequence-Based Amplification," Applied and Environmental Microbiology, 73(5), pp. 1457-1466, 2007.
Kievits et al., "NASBA™ Isothermal Enzymatic in vitro Nucleic Acid Amplification Optimized for the Diagnosis of HIV-1 Infection," Journald of Virological Methods, 35, pp. 273-286, 1991.
Kinoshita et al., "Multiple Primer Extension by DNA Polymerase on a Novel Plastic DNA Array Coated with a Biocompatible Polymer," Nucleic Acids Research, 35(1), pp. 1-9, 2007.
Pemov et al., "DNA Analysis with Multiplex Microarray-Enhanced PCR," Nucleic Acids Research, 33(2), pp. 1-9, 2005.
Schena et al., "Parallel Human Genome Analysis: Microarray-based Expression Monitoring of 1000 Genes," Proc. Natl. Acad. Sci. USA, 93(20), pp. 10614-10619, 1996.
European Search Report issued in corresponding EP 08845426.9 dated Jan. 5, 2011.

*Primary Examiner* — Kenneth R. Horlick
*Assistant Examiner* — David Thomas
(74) *Attorney, Agent, or Firm* — Kenneth H. Sonnenfeld; Margaret B. Brivanlou; King & Spalding

(57) ABSTRACT

[Object] It is to provide a method and a kit capable of detecting or quantifying a target RNA simply and rapidly from trace amounts of RNA in a sample, in a case such as when one or more kinds of pathogenic microorganisms are to be detected or quantified.
[Solving Means] The method comprises the steps of 1) synthesizing cDNA from a sample containing the target RNA using a liquid-phase primer having a promoter sequence and a reverse transcriptase to obtain a cDNA-RNA complex, 2) degrading the RNA of the complex, 3) synthesizing a double-stranded DNA via the cDNA obtained in the step 2) and the solid-phase primer, 4) synthesizing RNA from the double-stranded DNA, 5) synthesizing cDNA via the RNA obtained in the step 4) and the solid-phase primer to obtain a cDNA-RNA complex, 6) degrading the RNA of the complex obtained in step 5), 7) synthesizing a double-stranded DNA via the cDNA obtained in the step 6) and the liquid-phase primer, and 8) quantifying the double-stranded DNAs obtained in the steps 3) and 7). These steps can be performed in a single reaction solution.

22 Claims, 6 Drawing Sheets

SEQUENCE LISTING

```
<160> NUMBER OF SEQ ID NOS: 14

<210> SEQ ID NO 1
<211> LENGTH: 22
<212> TYPE: DNA
<213> ORGANISM: Artificial Sequence
<220> FEATURE:
<223> OTHER INFORMATION: primer

<400> SEQUENCE: 1
aaggtgcact tgcatcacta cc                                          22

<210> SEQ ID NO 2
<211> LENGTH: 23
<212> TYPE: DNA
<213> ORGANISM: Artificial Sequence
<220> FEATURE:
<223> OTHER INFORMATION: primer

<400> SEQUENCE: 2
tattatcgga agatgaaagt gcg                                         23

<210> SEQ ID NO 3
<211> LENGTH: 21
<212> TYPE: DNA
<213> ORGANISM: Artificial Sequence
<220> FEATURE:
<223> OTHER INFORMATION: primer

<400> SEQUENCE: 3
atggccaata caaacagtcg c                                           21

<210> SEQ ID NO 4
<211> LENGTH: 24
<212> TYPE: DNA
<213> ORGANISM: Artificial Sequence
<220> FEATURE:
<223> OTHER INFORMATION: primer

<400> SEQUENCE: 4
aactgtagaa atacagcttt ccgc                                        24

<210> SEQ ID NO 5
<211> LENGTH: 24
<212> TYPE: DNA
<213> ORGANISM: Artificial Sequence
<220> FEATURE:
```

-continued

<223> OTHER INFORMATION: primer

<400> SEQUENCE: 5
gaggagggtt gataggttaa gagc                     24

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
tcgagcggta gcacagagag                          20

<210> SEQ ID NO 7
<211> LENGTH: 22
<212> TYPE: DNA
<213> ORGANISM: Artificial Sequence
<220> FEATURE:
<223> OTHER INFORMATION: primer

<400> SEQUENCE: 7
atacgtcctg agggagaaag tg                       22

<210> SEQ ID NO 8
<211> LENGTH: 21
<212> TYPE: DNA
<213> ORGANISM: Artificial Sequence
<220> FEATURE:
<223> OTHER INFORMATION: primer

<400> SEQUENCE: 8
acccataagc cctgacgtta c                        21

<210> SEQ ID NO 9
<211> LENGTH: 18
<212> TYPE: DNA
<213> ORGANISM: Artificial Sequence
<220> FEATURE:
<223> OTHER INFORMATION: primer

<400> SEQUENCE: 9
gtattaccgc ggckgctg                            18

<210> SEQ ID NO 10
<211> LENGTH: 15
<212> TYPE: DNA
<213> ORGANISM: Artificial Sequence
<220> FEATURE:
<223> OTHER INFORMATION: primer

<400> SEQUENCE: 10
acgggcggtg tgtac                               15

<210> SEQ ID NO 11
<211> LENGTH: 23
<212> TYPE: DNA
<213> ORGANISM: Artificial Sequence
<220> FEATURE:
<223> OTHER INFORMATION: primer

<400> SEQUENCE: 11
taatacgact cactataggg cga                      23

<210> SEQ ID NO 12

```
<211> LENGTH: 24
<212> TYPE: DNA
<213> ORGANISM: Artificial Sequence
<220> FEATURE:
<223> OTHER INFORMATION: primer

<400> SEQUENCE: 12
ttattaaccc tcactaaagg gaag                                          24

<210> SEQ ID NO 13
<211> LENGTH: 23
<212> TYPE: DNA
<213> ORGANISM: Artificial Sequence
<220> FEATURE:
<223> OTHER INFORMATION: primer

<400> SEQUENCE: 13
atttaggtga cactatagaa tac                                           23

<210> SEQ ID NO 14
<211> LENGTH: 13
<212> TYPE: DNA
<213> ORGANISM: Artificial Sequence
<220> FEATURE:
<223> OTHER INFORMATION: primer

<400> SEQUENCE: 14
agaaggagca gga                                                      13
```

METHOD AND KIT FOR DETECTION/QUANTIFICATION OF TARGET RNA

TECHNICAL FIELD

The present invention relates to a method and a kit for detecting or quantifying a target RNA. More specifically, the present invention relates to a method for detecting or quantifying RNA, which method is a combination of a DNA microarray technique and nucleic-acid amplification technique; and to a kit for detecting or quantifying RNA.

BACKGROUND ART

As for identification of bacteria, for example, a method for identifying bacteria using DNA microarray technique has been developed, in addition to a conventionally-used identification method via culture and an identification method by staining or a method comprising measuring a substance associated with the bacterial metabolism such as ATP. Particularly, a technique comprising the steps of synthesizing as a probe nucleic acids having a nucleotide sequence which is specific to a gene sequence of certain bacteria, and fixing the probe on a substrate to allow the probe to hybridize with a gene amplified from a specimen is currently applied in various advanced ways. It is because this technique uses a nucleotide sequence specific to each bacterial species, and thus allows an accurate detection (see patent documents 1 to 3 and non-patent document 1).

One example of the quantitative-analysis method is a detection method by real-time PCR method. The real-time PCR method enables to perform a quantitative detection using trace amounts of sample, but the test takes time and in addition, the suitable number of cycles for quantification has to be found out for each template and primer for a highly-reproducible quantification, which results in a complicated operation.

Other method such as NASBA (Nucleic Acid Sequence Based Amplification) method which is for amplifying RNA-specific nucleic acids is proposed as a method capable of detecting a particular bacterial species or breed. NASBA method comprises amplifying an antisense RNA which is complementary to the intended RNA using two kinds of primers. Since with this method, it is possible to amplify nucleic acids in a short time using RNA as a template under the constant temperature of 41° C., the reaction can be performed at ordinary temperature without the need of a temperature-control device or the like. Further, the Tm value, etc. of the primer does not have to be taken into consideration, and this allows a simple detection of plural kinds of nucleic acids. Further, unlike RT-PCR, amplification and detection of RNA can be performed in the presence of DNA and thus possible false-positive cases due to dead bacteria can be eliminated by assessing viable bacteria. However, it has been said that while NASBA method is capable of detecting plural kinds of nucleic acids at the same time qualitatively and simply, a quantitative and simple detection is difficult with this method.

Meanwhile, pneumonia is in fourth place in the Japanese cause-specific death rates. It is frequently developed as a complication associated with an underlying disease such as cancer and is known as a disease affecting a very large number of individuals. Conventionally, a culture test which is performed as a search test for a microorganism that causes pneumonia (causative bacteria) takes at least several days and it takes nearly a week if a drug sensitivity test is further performed on the cultured causative bacteria. Therefore, this test method has not become a method which sufficiently contributes to the treatment selection. In a case of severe pneumonia which requires hospitalization in an intensive-care unit (ICU), a rapid and accurate determination of causative bacteria is very important in treatment selection, and it has been reported that an appropriate initial treatment definitely increases the life-saving rate of pneumonia patients. However, in reality, the actual state is that the treatment has to be carried out with the causative bacteria unidentified, because no techniques for identifying causative bacteria that may replace the culture method have been established yet. Consequently, use of antibiotics based on experience is unavoidable, which may potentially result in an appearance of drug-resistant bacteria.

Bacterial species that are frequently seen to cause pneumonia account for nearly 50% of the causative bacteria of pneumonia, and there are about 20 to 30 kinds of major causative bacteria including viruses. Some of these cannot be cultured by a common technique, and in many cases, it is difficult to determine the causative bacteria by culture method. Further, a conventional method for detecting microorganisms using DNA microarray technique was effective for detecting causative bacteria of pneumonia which cause pneumonia even with a very small infective dose, and for detecting plural kinds of bacteria at the same time, but such method had a problem in terms of a quantitative and highly-reproducible analysis. Particularly for pneumonia which needs to be treated by appropriately choosing an antibiotic depending on the bacterial amount, it is very important to detect plural kinds of causative bacteria of pneumonia at the same time and to quantitatively analyze the detected signals. Further, optimal therapeutic agents differ depending on the kind of the causative bacteria, but in actual state, it is unavoidable to start the treatment before determining the causative bacteria from the viewpoint of medical ethics. In order to solve these problems, the development of a technique capable of detecting specific bacteria rapidly and quantitatively from among plural bacterial species has been awaited.

Patent Document 1: Japanese Laid-Open Patent Application No. 2002-512688
Patent Document 2: Japanese Laid-Open Patent Application No. 2006-025791
Patent Document 3: Japanese Laid-Open Patent Application No. 2006-061155
Non-Patent Document 1: Schena M. et al. (1996) Proc. Natl. Acad. Sci. USA. 93(20): 10614-9

DISCLOSURE OF THE INVENTION

Object to be Solved by the Invention

The object of the present invention is to provide a method and a kit capable of detecting or quantifying a target RNA simply and rapidly from trace amounts of RNA in a sample, in a case such as when one or more kinds of pathogenic microorganisms are to be detected or quantified.

Means to Solve the Object

For detecting trace amounts of genes of plural kinds of bacteria, the present inventors already focused on using a 16S rRNA sequence as a primer, which is one of the constitutional components of ribosome, a protein-synthesis organelle. The nucleotide sequence of 16S rRNA can be obtained from all bacteria and it is a characteristic of 16S rRNAs that they have a common nucleotide-sequence portion and a bacteria-specific nucleotide-sequence portion. Therefore, a quantitative detection method comprising designing a primer for detecting a bacteria-specific sequence by utilizing the above property, amplifying a plurality of genes at the same time using multiplex PCR method, and quantitatively detecting the amplified product by PCR method using a microarray was developed to propose a method for detecting the genes of 10 species of causative bacteria of pneumonia (jointly developed by Yamaguchi University and Sumitomo Bakelite Co., Ltd., applied for a patent: Japanese Patent Application No. 2007-207966). However, this method requires a DNA amplifier and microarray scanner, which makes it difficult for many small and medium-sized hospitals and clinics to perform the examination. In light of this actual state and in order to develop a diagnostic device that allows a simple examination without using a special device, the present inventors first developed the world's first method for amplifying and quantifying nucleic acids, which enables a simultaneous amplification and quantitative detection of a double-stranded DNA produced in the process of NASBA method, comprising amplifying RNA at a constant temperature using three kinds of primers, liquid-phase primers and a solid-phase primer, in the measurement system that uses a fluorescence measurement device. However, this detection system only confirmed that it can detect one species of bacteria. Further, a reverse-transcription primer used in a conventional NASBA method is a primer for converting RNA in a clinical sample to DNA, and thus it is important to set the concentration of a primer because the primer is added into the solution. The setting of concentration in a new gene-detection method depends on how many kinds of reverse-transcription primers are to be mixed. If the number of the intended genes to be detected increases, the number of reverse-transcription primers has to be increased. Since drug-resistant genes do not share a common region, reverse-transcription primers had to be added in the same number as the drug-resistant genes. In the present case, the present inventors arrived at the idea that plural kinds of nucleic acids having a target nucleotide sequence can be detected at a time using a primer set used in multiplex PCR method, and then tried to detect or quantify RNA using a reagent used in NASBA method and a plurality of primers. However, the amplification of multiple bacterial species with the NASBA reagent caused many cross-reactions and no favorable results have been obtained. Consequently, the present inventors have found that many kinds of DNA sequences in a sample specimen can be simply detected or quantified in a short time by amplifying a double-stranded DNA produced in the process of NASBA method on a well-type microarray substrate using many kinds of primers, and thus completed the present invention.

More specifically, the present invention relates to [1] a method for detecting or quantifying a target RNA, comprising the following steps (a) to (j):
(a) a step of fixing a 5' end of a primer comprising a DNA sequence corresponding to a 5'-side target specific sequence of the target RNA on a surface of a substrate to prepare a solid-phase DNA (+) primer;
(b) a step of preparing a liquid-phase cDNA (−) primer wherein an RNA-polymerase promoter sequence is added via a tag sequence to a 5'-end side of a primer comprising a cDNA sequence which is complementary to a 3'-side sequence of the target RNA, and a liquid-phase universal primer wherein an RNA-polymerase promoter sequence is added to a 5' end of a tag sequence;
(c) a step of preparing a sample RNA comprising a 3'-side sequence and 5'-side target specific sequence of the target RNA;
(d) a step of allowing the liquid-phase cDNA (−) primer prepared in step (b) to contact with the sample RNA strand prepared in step (c) in a liquid phase to hybridize the liquid-phase cDNA (−) primer and the sample RNA, and then extending a DNA (−) strand by a reverse transcriptase to prepare a cDNA strand-RNA strand complex;
(e) a step of allowing an RNase that specifically degrades an RNA strand in a DNA strand-RNA strand complex, to act on the cDNA strand-RNA strand complex prepared in step (d) to prepare a single-stranded DNA (−);
(f) a step of allowing the single-stranded DNA (−) prepared in step (e) to contact with the solid-phase DNA (+) primer prepared in step (a) in a liquid phase to hybridize the single-stranded DNA (−) and the solid-phase DNA (+) primer, and then extending a DNA (+) strand by an enzyme having a DNA-dependent DNA-polymerase activating capacity to prepare a double-stranded DNA;
(g) a step of allowing an RNA polymerase to act on the double-stranded DNA prepared in step (f) to amplify a single-stranded RNA (−) utilizing an RNA-polymerase promoter sequence derived form the DNA (−) strand, hybridizing an amplified single-stranded RNA (−) and a solid-phase DNA (+) primer, and then extending a DNA (+) strand by a reverse transcriptase to prepare a cDNA strand-RNA strand complex;
(h) a step of allowing an RNase that specifically degrades an RNA strand in a DNA strand-RNA strand complex, to act on the cDNA strand-RNA strand complex prepared in step (g) to prepare a solid-phase single-stranded DNA (+);
(i) a step of allowing the solid-phase single-stranded DNA (+) prepared in step (h) to contact with the liquid-phase universal primer prepared in step (b) in a liquid phase to hybridize the single-stranded DNA (+) and the liquid-phase universal primer, and then extending a DNA (−) strand by an enzyme having a DNA-dependent DNA-polymerase activating capacity to prepare a double-stranded DNA; and
(j) a step of quantifying the double-stranded DNAs prepared in step (f) and step (i).

The present invention further relates to [2] the detection or quantification method according to [1], wherein step (g) to step (i) are repeated twice or more; [3] the detection or quantification method according to [1] or [2], wherein step (d) to step (j) are performed in a single reaction solution; [4] the detection or quantification method according to any one of [1] to [3], wherein a plurality of target RNAs are detected or quantified on a same substrate; [5] the detection or quantification method according to any one of [1] to [4], wherein the tag sequence is sequence AGAAGG, or AGAAGG to which any 7 nucleotides rich in AG are further added; [6] the detection or quantification method according to any one of [1] to [4], wherein the tag sequence is AGAAGGAGCAGGA; [7] the detection or quantification method according to any one of [1] to [6], wherein a liquid-phase universal primer concentration is 10 times or more than a liquid-phase cDNA (−) primer concentration; [8] the detection or quantification method according to any one of [1] to [7], wherein a liquid-phase universal primer or liquid-phase chimeric primer, in which the RNA-polymerase promoter sequence is a labeled promoter sequence, is used; [9] the detection or quantification method according to [8], wherein the labeled promoter sequence is a biotinylated promoter sequence; [10] the detection or quantification method according to any one of [1] to [7], wherein step (i) is performed in the presence of a labeling reagent; [11] the detection or quantification method according to [10], wherein the labeling reagent is a fluorescent dye; [12] the detection or quantification method according to any one of [1] to [11], wherein the reverse transcriptase is used as an enzyme having a DNA-dependent DNA-polymerase activating capacity; [13] the detection or quantification method according to any one of [1] to [12], wherein the target RNA is a bacteria-specific RNA strand in 16S rRNA; and [14] a method for detecting or quantifying one or more pathogenic microorganisms using the method for detecting or quantifying RNA according to any one of [1] to [13].

The present invention further relates to [15] a kit for detecting or quantifying RNA, comprising a solid-phase DNA (+) primer wherein a 5' end of the primer comprising a 5'-side target specific sequence of a target RNA is fixed on a surface of a substrate; a liquid-phase cDNA (−) primer wherein an RNA-polymerase promoter sequence is added via a tag sequence to a 5'-end side of the primer comprising a' cDNA sequence which is complementary to a 3'-side sequence of the target RNA; a liquid-phase universal primer wherein an RNA-polymerase promoter sequence is added to a 5'-end side of a tag sequence; a reverse transcriptase; an RNA polymerase; and an RNase that specifically degrades an RNA strand in a DNA strand-RNA strand complex; [16] the kit for detecting or quantifying RNA according to [15], wherein the tag sequence is sequence AGAAGG, or AGAAGG to which any 7 nucleotides rich in AG are further added; [17] the kit for detecting or quantifying RNA according to [15], wherein the tag sequence is AGAAGGAGCAGGA; [18] the kit for detecting or quantifying RNA according to any one of [15] to [17], wherein the RNA-polymerase promoter sequence is a labeled promoter sequence; [19] the kit for detecting or quantifying RNA according to [18], wherein the labeled promoter sequence is a biotinylated promoter sequence; [20] the kit for detecting or quantifying RNA according to any one of [15] to [17], further comprising a labeling reagent; [21] the kit for detecting or quantifying RNA according to [20], wherein the labeling reagent is a fluorescent dye; [22] the kit for detecting or quantifying RNA according to any one of [15] to [21], further comprising a DNA-dependent DNA polymerase; and [23] the kit for detecting or quantifying RNA according to any one of [15] to [22], wherein the target RNA is a bacteria-specific RNA strand in 16S rRNA.

Effect of the Invention

According to the method for quantifying nucleic acids developed by the present invention, nucleic acids are amplified quantitatively via a universal primer, and even if the nucleic-acid amplification efficiencies are different depending on the primers used in the nucleic-acid amplification, uniform amplification efficiencies are achieved between the primers by amplifying nucleic acids using the same universal primer, and thus a quantitative analysis by nucleic-acid amplification has become possible. As stated, by amplifying nucleic acids using a universal primer, a new microarray technique that enables a simple and quantitative detection without performing a real-time PCR can be provided. Further, even when detecting new pathogenic bacteria, the detection is possible by adding a solid-phase primer having a sequence which is specific to the pathogenic bacteria. Therefore, the present method is original and versatile compared to a conventional gene-detection method that can detect limited bacterial species. Further, according to the method for quantifying nucleic acids of the present invention, detected signals can be analyzed quantitatively and therefore, it is effective for, for example, a detection of causative bacteria that causes different symptoms according to the infective dose and of plural kinds of causative bacteria. In particular, the method of the present invention enables an accurate detection or quantification of a number of drug-resistant genes at the same time in a short time, and thus paves way to the construction of a new gene-quantification-detection system. Further, the gene-detection system using the method for quantifying nucleic acids of the present invention can be utilized as a reagent for a simple clinical diagnostic test for choosing an appropriate therapy against pathogenic microorganisms that are difficult to cultivate such as *chlamydia* and *rickettsia*, and causative bacteria of a hospital-acquired infection such as drug-resistant bacteria. Further, the present invention uses synthetic resin as a substrate, and thereby provides a highly versatile system that is easy to use and can be processed appropriately according to the detection device.

BRIEF DESCRIPTION OF DRAWINGS

FIG. 6 i) shows a liquid-phase chimeric primer hybridized to the 3' side of the target RNA in step (d); ii) shows a cDNA strand-RNA strand complex synthesized by a reverse transcription; iii) shows a pattern diagram of the reaction in step (e); iv) shows a pattern diagram of the reaction in step (f); v) shows how the antisense RNA is amplified in step (g); vi) shows how an amplified antisense RNA hybridizes with a solid-phase DNA (+) primer in step (g); vii) shows a cDNA strand-RNA strand complex in step (g); viii) shows how the RNA strand of the cDNA strand-RNA strand complex is degraded in step (h); ix) shows a pattern diagram of the reaction in step (i), wherein a single-stranded DNA (+) is hybridized with a liquid-phase cDNA primer (−) or liquid-phase universal primer; and x) shows a labeled double-stranded DNA in step (i) and how the single-stranded RNA (−) of step (g) is amplified following step (i).

BEST MODE OF CARRYING OUT THE INVENTION

The method for detecting or quantifying a target RNA of the present invention is not particularly limited as long as it is a method comprising the following steps (a) to (j). The term "target RNA" means RNA which is a subject of identification and/or quantification, and bacteria-specific RNA strand in 16S rRNA, etc. can be exemplified preferably as stated below:

(a) a step of fixing a 5' end of a primer comprising a DNA sequence corresponding to a 5'-side target specific sequence of the target RNA on a surface of a substrate to prepare a solid-phase DNA (+) primer;

(b) a step of adding an RNA-polymerase promoter sequence to a 5'-end side of a primer comprising a cDNA sequence which is complementary to a 3'-side sequence of the target RNA to prepare a liquid-phase cDNA (−) primer;

(b') a step of preparing as needed a liquid-phase universal primer wherein an RNA-polymerase promoter sequence is added to a 5' end of a tag sequence;

(c) a step of preparing a sample RNA comprising a 3'-side sequence and 5'-side target specific sequence of the target RNA;

(d) a step of allowing the liquid-phase cDNA (−) primer prepared in step (b) to contact with the sample RNA strand prepared in step (c) in a liquid phase to hybridize the liquid-phase cDNA (−) primer and the sample RNA, and then extending a DNA (−) strand by a reverse transcriptase to prepare a cDNA strand-RNA strand complex;

(e) a step of allowing an RNase that specifically degrades an RNA strand in a DNA strand-RNA strand complex, to act on the cDNA strand-RNA strand complex prepared in step (d) to prepare a single-stranded DNA (−);

f) a step of allowing the single-stranded DNA (−) prepared in step (e) to contact with the solid-phase DNA (+) primer prepared in step (a) in a liquid phase to hybridize the single-stranded DNA (−) and the solid-phase DNA (+) primer, and then extending a DNA (+) strand by an enzyme having a DNA-dependent DNA-polymerase activating capacity to prepare a double-stranded DNA;

(g) a step of allowing an RNA polymerase to act on the double-stranded DNA prepared in step (f) to amplify a single-stranded RNA (−) utilizing an RNA-polymerase promoter sequence derived form the DNA (−) strand, hybridizing an amplified single-stranded RNA (−) and a solid-phase DNA (+) primer, and then extending a DNA (+) strand by a reverse transcriptase to prepare a cDNA strand-RNA strand complex;

(h) a step of allowing an RNase that specifically degrades the RNA strand in a DNA strand-RNA strand complex, to act on the cDNA strand-RNA strand complex prepared in step (g) to prepare a solid-phase single-stranded DNA (+);

(i) a step of allowing the solid-phase single-stranded DNA (+) prepared in step (h) to contact with the liquid-phase cDNA (−) primer prepared in step (b) or with the liquid-phase universal primer prepared in step (b') in a liquid phase to hybridize the single-stranded DNA (+) and the liquid-phase cDNA (−) primer or the liquid-phase universal primer, and then extending a DNA (−) strand by an enzyme having a DNA-dependent DNA-polymerase activating capacity to prepare a double-stranded DNA; and (j) a step of quantifying the double-stranded DNAs prepared in the step (f) and step (i).

The sample in the above step (c) is not particularly limited as long as it comprises RNA of a cell or tissue of a microorganism, animal, plant, etc., for example, RNA including mRNA and rRNA such as 16S rRNA and 23S rRNA in a prokaryote, and 18S rRNA and 28S rRNA in a eukaryote. Further examples include a biological sample such as a cell lysate, a culture obtained from a biological sample, and synthetic RNAs obtained by RNA amplification. Among these, 16S rRNA in a prokaryote and 18S rRNA in a eukaryote can be preferably exemplified, since it has been revealed that these RNAs have a suitable gene length, are present in a cell in a large amount, and have a highly conservative sequence, while there exists a relatively mutation-prone portion. Further, examples of the above microorganism include pathogenic microorganisms that are difficult to cultivate such as *chlamydia* and *rickettsia*, in addition to MRSA and pathogenic bacteria of pneumonia whose causative bacteria are difficult to identify. Further, the phrase "to prepare a sample RNA comprising a 5'-side sequence and 3'-side target specific sequence of the target RNA" means to extract RNA from samples using guanidine thiocyanate and a commercially available kit, etc., and appropriately cleaving the extracted RNA, thereby to prepare one or more RNAs comprising a 5'-side sequence and 3'-side target specific sequence of the target RNA. However, the above phrase also includes the case where samples do not comprise these target RNAs, for convenience sake.

The 5'-side target specific sequence of the target RNA in the above step (a) is not particularly limited as long as it is present on the 5'-side of the target RNA and is a sequence specific to the target RNA, which enables the detection or quantification of the target RNA distinguishably from the rest of RNAs contained in a sample. Such 5'-side sequence of the target RNA can be selected using a known database advantageously, or in other way by: performing amplification of RNA by PCR method using a primer, and RNA of a specific bacterial strain which is the subject of detection as a template; purifying the amplified fragments with a commercially available purification column (QIAGEN), etc.; determining the sequence by four-color dye-terminator method with ABI PRIZM™ 377 Genetic Analyzer (P. E. Biosystems), etc.; and thereby selecting the 5'-side sequence of the target RNA from the sequence information.

Specific examples of the 5'-side target specific sequence of the target RNA include the nucleotide sequence at positions 202 to 223 shown by SEQ ID NO: 1 of the sequence listing, assuming that the 1st position is the transcription-initiation site of the gene region encoding 16S rRNA of *Streptococcus pneumoniae*; the nucleotide sequence at positions 165 to 187 shown by SEQ ID NO: 2, assuming that the 1st position is the transcription-initiation site of the gene region encoding 16S rRNA of *Hemophilus influenzae*; the nucleotide sequence at positions 1225 to 1245 shown by SEQ ID NO: 3, assuming that the 1st position is the transcription-initiation site of the gene region encoding 16S rRNA of *Mycoplasma pneumoniae*; the nucleotide sequence at positions 994 to 1017 shown by SEQ ID NO: 4, assuming that the 1st position is the transcription-initiation site of the gene region encoding 16S rRNA of *Chlamydia pneumoniae*; the nucleotide sequence at positions 436 to 459 shown by SEQ ID NO: 5, assuming that the 1st position is the transcription-initiation site of the gene region encoding 16S rRNA of *Legionella* ssp.; the nucleotide sequence at positions 52 to 71 shown by SEQ ID NO: 6, assuming that the 1st position is the transcription-initiation site of the gene region encoding 16S rRNA of *Klebsiella pneumoniae*; the nucleotide sequence at positions 164 to 185 shown by SEQ ID NO: 7, assuming that the 1st position is the transcription-initiation site of the gene region encoding 16S rRNA of *P. aereruginosae*; and the nucleotide sequence at positions 453 to 473 shown by SEQ ID NO: 8, assuming that the 1st position is the transcription-initiation site of the gene region encoding 16S rRNA of *Moraxella catarrhalis*. These can be preferably used for the detection for identifying causative bacteria of pneumonia.

Further, the phrase "a DNA sequence corresponding to the 5'-side target specific sequence of the target RNA" means a DNA sequence wherein U (uridine) in the 5'-side RNA sequence of the target RNA is replaced by T (thymine). A primer comprising a DNA sequence corresponding to the 5'-side target specific sequence of the target RNA can be prepared as a solid-phase DNA (+) primer consisting of a primer fixed on the substrate, by fixing the 5' end of the primer on the surface of the substrate. In the solid-phase DNA (+) primer, there exists a DNA sequence that corresponds to the target specific sequence of the 5'-side of the target RNA, and thus the target RNA can be identified in a substrate-position specific manner. For example, when using a substrate having a plurality of wells, a *Streptococcus pneumoniae*-specific sequence is fixed on well #1, a *Hemophilus influenzae*-specific sequence on well #2, and a *Mycoplasma pneumoniae*-specific sequence on well #3. This enables the detection or quantification of the target RNA based on the quantification result of a double-stranded DNA of each well in step (j). In this manner, when only one kind of primer is fixed on the bottom surface of individual wells, gene amplification is curried out only in the corresponding well and thereby the detection or quantification of a target RNA is enabled even if a common reaction solution (amplification reagent, chimeric primer, universal primer and a mixture of sample RNAs) is used.

To achieve a higher affinity between the primer and the surface of a substrate, a linker moiety can be introduced into the 5'-side of the DNA sequence of the primer. For example, an amino group is preferred as a linker moiety to be introduced in that, when there is an active ester group on the surface of the substrate, the amino group can enhance the reactivity with the active ester group and thus allows an efficient and solid fixing on the surface of the substrate. Further, the material of the substrate is not particularly limited as long as it is insoluble in water and can bind the primer. Examples include a linear polyolefin resin, cyclic polyolefin resin, and fluorine-containing resin, while use of cyclic polyolefin is preferred in terms of superior chemical resistance, low fluorescence, transparency and moldability.

Further, the shape of the substrate is not particularly limited as long as the shape allows a simultaneous quantification of plural kinds of nucleic acids. Examples include a substrate having a film-like, tube-like, or plate-like shape, and specifically, a multiplate such as a 96-well plate can be preferably exemplified. When the substrate has a multiplate-like shape, the surface of the substrate is preferably made by microfabrication into a structure for the use as a small microplate. In this case, it is preferred that a plurality of concave parts are formed on the surface of the substrate so that the solid-phase primers are fixed at the concave parts, because the formed concave parts allow the efficient hybridization of the single-stranded RNA (−) synthesized in step (g) with the solid-phase DNA (+) primer. A preferred concave part is a well with a depth of 150 to 250 μm and a bottom-part diameter of 0.5 to 1.5 mm.

The embodiment of fixing a primer to the surface of a substrate is not particularly limited, and examples of the embodiment include a covalent bonding, ion bonding, physical adsorption, and binding a solid-phase primer to a gel, while a covalent bonding can be preferably exemplified. Specific examples include a method of forming a covalent bonding between the primer wherein, when there exist on the surface of the substrate to be used a high-molecular substance comprising a first unit having a group derived from ester phosphate constituting the hydrophilic portion of phospholipid and a second unit having a carboxylic-acid derivative, a part of the active ester group contained in the high-molecular substance reacts with a primer in which an amino group has been introduced as a linker on the 5'-side of the primer. Herein, the first unit functions to inhibit non-specific adsorption of the primer and as for the second unit, the carboxylic-acid derivative of the second unit functions to chemically immobilize the primer. The primer is covalently bound at the position of the carboxylic-acid derivative of the coating layer consisting of the high-molecular substance, and thus immobilized on the surface of the substrate.

Figure 1:
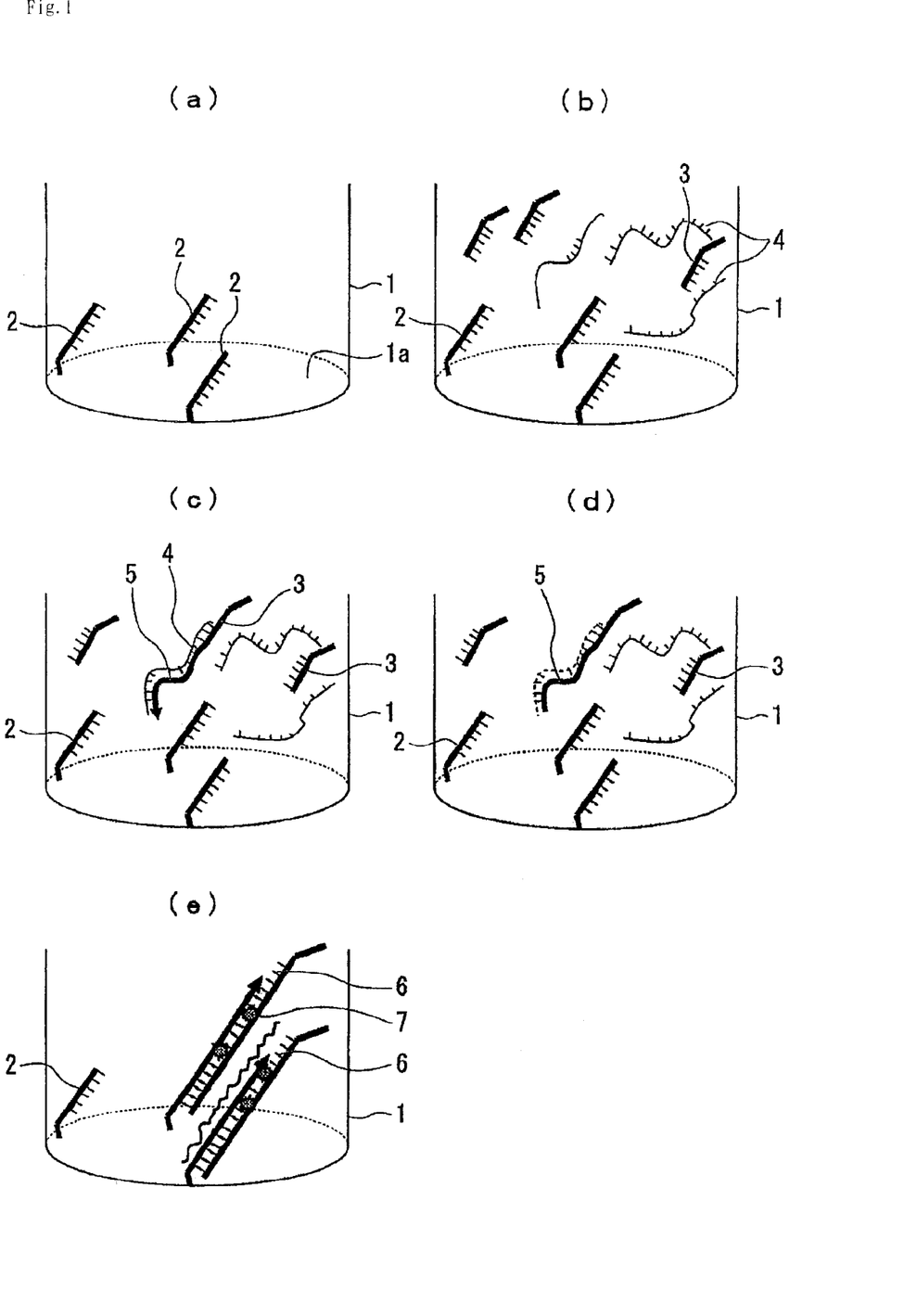
FIG. 1 This figure shows pattern diagrams of steps (a) to (f). (a) shows that solid-phase DNA (+) primers 2 are fixed on surface 1*a* of substrate 1; (b) and (c) show how the reaction is initiated after solid-phase DNA (+) primers 2 are fixed on surface 1*a* of substrate 1 in step (d); (d) shows a pattern diagram of the reaction in step (e); and (e) shows a pattern diagram of the reaction in step (f).

When fixing a solid-phase primer by a covalent bonding, the primer is preferably fixed in a standing position as shown in FIG. 1(a), so as to make it easier for a solid-phase DNA (+) primer to capture a single-stranded RNA (−) which was produced in step (g) by utilizing an RNA-polymerase promoter sequence derived from a DNA (−) strand, and for a single-stranded DNA (−) prepared in step (f) to bind to the solid-phase DNA (+) primer using the solid-phase primer as a starting point. Examples of such method for fixing a solid-phase primer include a method wherein primers are spread using a solution in which primers are dissolved or dispersed. The pH of the solution wherein primers are dissolved or dispersed is preferably neutral to alkaline, because this enables the primers to project from the surface of the substrate in the well, and is more preferably at least 7.6. The specific example of the solution includes TE buffer (pH 8.0).

Further, in order to eliminate primers that have not been immobilized on the surface of a substrate after the spreading, it is preferred to wash with pure water, buffer solution, etc. After the washing, active esters on the surface of the substrate, other than those used for immobilizing the primers, are preferably inactivated by treatment with an alkaline compound or a compound having a primary amino group. Examples of the alkaline compound include sodium hydroxide, potassium hydroxide, sodium carbonate, sodium hydrogen carbonate, disodium hydrogen phosphate, calcium hydroxide, magnesium hydroxide, sodium borate, lithium hydroxide, and potassium phosphate. Examples of the compound having a primary amino group include glycine, 9-aminoaquadine, aminobutanol, 4-aminobutyric acid, aminocaprylic acid, aminoethanol, 5-amino-2,3-dihydro-1,4-pentanol, aminoethanethiol hydrochloride, aminoethanethiol sulfuric acid, 2-(2-aminoethylamino)ethanol, 2-aminoethyl dihydrogen phosphate, aminoethyl hydrogen sulfate, 4-(2-aminoethyl) morpholine, 5-aminofluorescein, 6-aminohexanoic acid, aminohexyl cellulose, p-aminohippuric acid, 2-amino-2-hydroxymethyl-1,3-propanediol, 5-aminoisophthalic acid, aminomethane, aminophenol, 2-aminooctane, 2-aminooctanoic acid, 1-amino-2-propanol, 3-amino-1-propanol, 3-aminopropene, 3-aminopropionitrile, aminopyridine, 11-aminoundecanoic acid, aminosalicylic acid, aminoquinoline, 4-aminophthalonitrile, 3-aminophthalimide, p-aminopropiophenone, aminophenylacetic acid, and aminonaphthalene, while among which, aminoethanol and glycine are preferred.

Further, to achieve a secure fixation of a solid-phase primer used in the present invention to a substrate, it is more preferred to further immobilize the primer by heating at 75 to 85° C. for 1 hour after washing and then irradiating with 120/mJ/cm$^2$ UV following the heat treatment.

The 3'-side sequence of the target RNA in the above step (b) is not particularly limited as long as it is a sequence present on the 3' side of the target RNA, and it may be a target specific sequence on the 3' side. Meanwhile, by allowing the primer to include a sequence common to plural kinds of target RNAs (for example, a common conserved region), a liquid-phase cDNA (−) primer such as a common liquid-phase chimeric primer can be used when detecting or quantifying plural kinds of target RNAs, which results in a simple production of the primer advantageously. For example, due to a possible non-specific reaction caused by an increased number of kinds of liquid-phase cDNA (−) primer, it is preferred to design the liquid-phase cDNA (−) primer by trying as much as possible to select a common-region sequence of RNA sequences in a sample, for example, to select a common-region sequence of 16S RNAs of bacteria to be used for the detection or quantification. Specific examples thereof include the nucleotide sequence at positions 502 to 519 shown by SEQ ID NO: 9 of the sequence listing, assuming that the 1st position is the transcription-initiation site of the gene region encoding 16S rRNA of *Streptococcus pneumoniae, Hemophilus influenzae, Legionella* spp., *Klebsiella pneumoniae, Pseudomonas aeruginosae*, and *Moraxella catarrahalis*; and the nucleotide sequence at positions 1378 to 1392 shown by SEQ ID NO: 10, assuming that the 1st position is the transcription-initiation site of the gene region encoding 16S rRNA of *Mycoplasma pneumoniae* and *Chlamydia pneumoniae*. These can be advantageously used in the production of a liquid-phase cDNA (−) primer for identifying causative bacteria of pneumonia.

Further, a liquid-phase cDNA (−) primer can be prepared by adding an RNA-polymerase promoter sequence to the 5'-end side of a primer comprising a cDNA sequence which is complementary to the 3'-side sequence of the target RNA. Meanwhile, it is preferred to make a liquid-phase chimeric primer wherein an RNA-polymerase promoter sequence is added via a tag sequence to the 5'-end side of the primer comprising a cDNA sequence which is complementary to the 3'-side sequence of the target RNA. The above liquid-phase cDNA (−) primer, preferably a liquid-phase chimeric primer, is used in step (d), while in step (i), a liquid-phase universal primer is preferably used. The liquid-phase universal primer cannot be used in step (d). However, step (b') becomes an essential step when the liquid-phase universal primer is to be used in step (i), and the liquid-phase universal primer in step (b') can be prepared by adding an RNA-polymerase promoter sequence to the 5' end of the tag sequence. Further, the RNA-polymerase promoter sequence in the liquid-phase universal primer and the RNA-polymerase promoter sequence in the liquid-phase cDNA (−) primer may be the same or different.

A liquid-phase universal primer without the 3'-side sequence of the target RNA has a common sequence (a sequence wherein an RNA-polymerase promoter sequence is further added to the 5' end of a tag sequence), and therefore can unify the gene-amplification efficiencies which differ depending on 3'-side sequences, regardless of the difference of target RNAs. For example, by decreasing the mixing amount of a liquid-phase chimeric primer to the minimum that can cause an RNA-amplification reaction while increasing the amount of a liquid-phase universal primer, the amplification reaction is replaced by the reaction proceeded solely by the universal primer. As a result, RNA amplification is caused by the binding of RNA polymerase to a promoter sequence, and thereby the gene-amplification efficiencies which differ depending on 3'-side sequences can be unified. Therefore, when using a liquid-phase universal primer in step (i), the concentration of the liquid-phase universal primer is preferably equal to or more than 10 times, for example, 10 to 100 times, of the concentration of a liquid-phase cDNA (−) primer such as a liquid-phase chimeric primer.

The promoter sequence of the liquid-phase chimeric primer or liquid-phase universal primer is preferably a promoter sequence wherein an RNA polymerase that can specifically amplify RNA via the promoter is present. A known promoter can be selected and used as desired, and examples include the promoter sequence of T7 polymerase (5'-TAATACGACTCACTATAGGGCGA-3') [SEQ ID NO: 11], the promoter sequence of T3RNA polymerase (5'-TTAT-TAACCCTCACTAAAGGGAAG-3') [SEQ ID NO: 12], and the promoter sequence of SP6RNA polymerase (5'-ATT-TAGGTGACACTATAGAATAC-3') [SEQ ID NO: 13]. Among these, the promoter sequence of T7 polymerase is preferred in terms of high RNA-amplification efficiency. A liquid-phase cDNA (−) primer can be synthesized using a DNA synthesizer according a standard procedure. Further, as a promoter sequence, a labeled promoter sequence can be used advantageously so that a simple detection or quantification of a double-stranded DNA in step (j) can be performed utilizing this label. Examples of the labeling substance for the labeling include enzymes such as peroxidase (for example, horseradish peroxidase), alkaline phosphatase, β-D-galactosidase, glucose oxidase, glucose-6-phosphate dehydrogenase, alcohol dehydrogenase, malate dehydrogenase, penicillinase, catalase, apo-glucose oxidase, urease, luciferase and acetylcholinesterase; fluorescent substances such as fluorosceinisothiocyanate, phycobiliprotein, rare earth metal chelate, dansyl chloride, and tetramethylrhodamine isothiocyanate; radioisotopes such as $^{3}H$, $^{14}C$, $^{125}I$ and $^{131}I$; biotin, avidin, and a chemiluminescent substance. For example, when using a biotinylated promoter sequence, quantification can be performed using avidin or enzymatically modified avidin. For example, when using streptavidin-β-galactosidase as a biotin substrate, 4-methyl-umbelliferyl-D-galactosidase can be used as a chromogenic substance. Further, when using streptavidin-alkaline phosphatase as a biotin substrate, quantification can be performed by observing a blue insoluble compound produced by the interaction of 5-bromo-4-chloro-3-indole-phosphoric acid and 4-nitro blue tetrazolium chloride as chromogenic substances.

A preferred tag sequence in the liquid-phase chimeric primer and liquid-phase universal primer is a sequence which does not hybridize with a 3'-side sequence or RNA-polymerase promoter sequence, that consists of 1 to 20 nucleotides, preferably 5 to 15 nucleotides, and preferably rich in AG. Specifically, the sequence AGAAGG, or AGAAGG to which any 7 nucleotides rich in AG are further added, for example, AGAAGGAGCAGGA [SEQ ID NO: 14] can be exemplified.

In the present invention, the number of base pairs amplified by using a primer set constituted by a solid-phase DNA (+) primer and liquid-phase cDNA (−) primer can be set as desired by considering the nucleotide sequence of nucleic acids used as a template, the activity of the polymerase used, etc. However, if it is too long, there is a risk of lowering the amplification accuracy, and therefore the preferred length is 50 to 500 base pairs.

Figure 2:
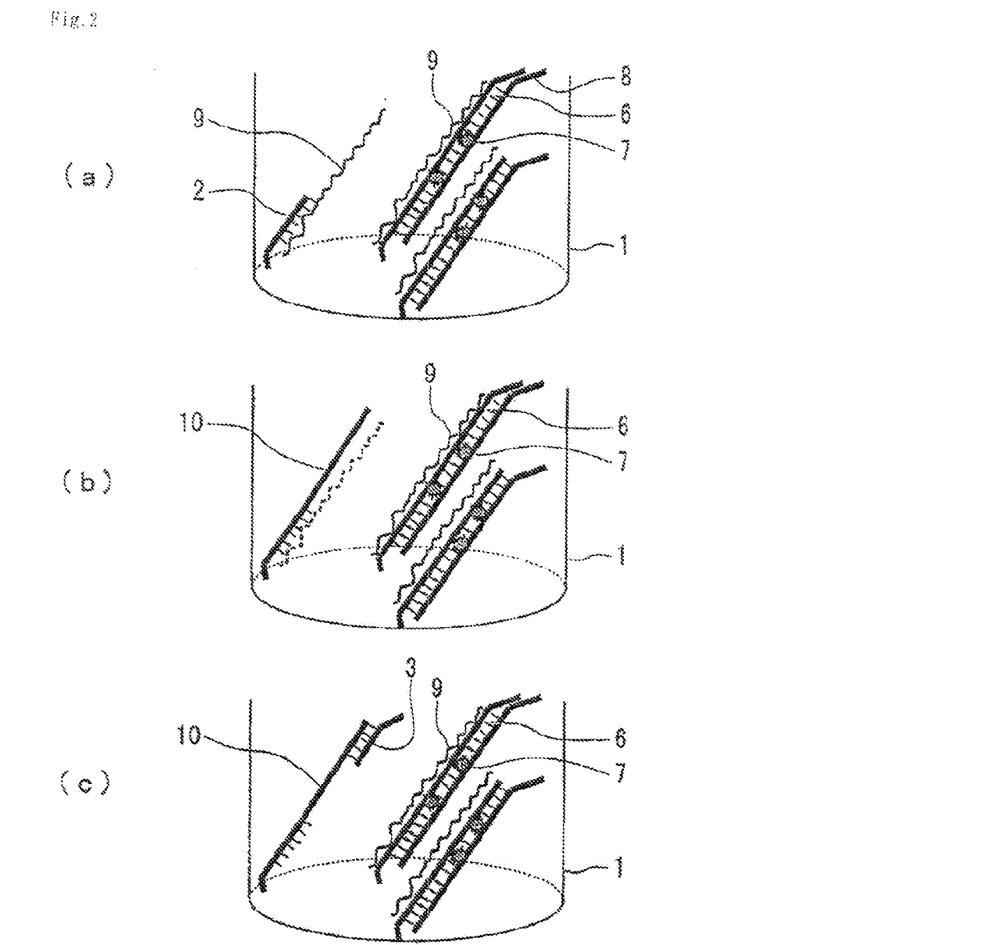
FIG. 2 This figure shows pattern diagrams of steps (g) to (i). (a) shows a pattern diagram of the reaction in step (g), wherein single-stranded RNAs 9 are synthesized via promoter sequences 8 present on double-stranded DNAs 6, that are then hybridized with solid-phase DNA (+) primers 2; (b) shows the reaction in step (h), wherein cDNA strands (+) 10 are synthesized via solid-phase DNA (+) primers 2 to produce cDNA strand-RNA strand complexes, and then the RNA strands of the cDNA strand-RNA strand complexes are degraded to obtain single-stranded DNAs (+) 10; and (c) shows a pattern diagram of the reaction in step (i), wherein solid-phase single-stranded DNAs (+) 10 are hybridized with liquid-phase cDNA (−) primers or liquid-phase universal primers 3*b* to prepare double-stranded DNAs.
Figure 6:
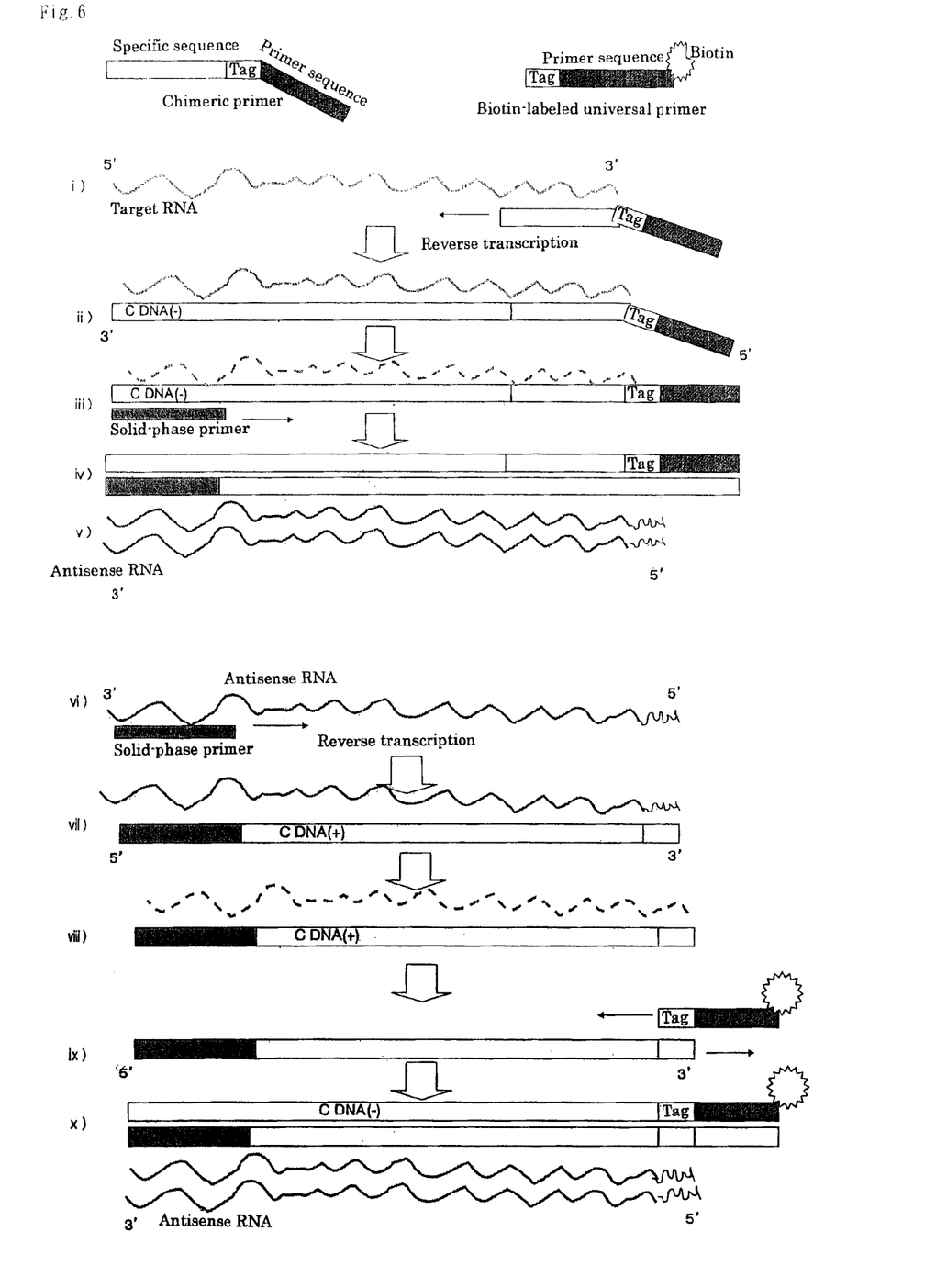

Steps (d) to (j) of the method for detecting or quantifying a target RNA using a liquid-phase chimeric primer in step (d) and using a liquid-phase universal primer in step (i) will be explained hereinbelow with reference to FIGS. 1 and 2 and FIG. 6. FIGS. 1 and 2 show a method using an unlabeled liquid-phase universal primer in the presence of a labeling reagent, and FIG. 6 shows a method using a labeled liquid-phase universal primer. As can be seen from the following explanation, step (d) to step (j) can be performed in a single reaction solution.

Step (d) comprises allowing the liquid-phase chimeric primer prepared in step (b) to contact with the sample RNA strand prepared in step (c) in a liquid phase to hybridize the liquid phase and the sample RNA, and then extending a cDNA (−) strand from the 5' side to the 3' side by a reverse transcriptase using the RNA strand contained in the sample as a template to prepare a cDNA strand-RNA strand complex. For example, the cDNA strand-RNA strand complex can be synthesized by allowing a reverse transcriptase to act in the presence of deoxynucleotides. Examples of the reverse transcriptase include AMV (Avian Myeloblastosys Virus) reverse transcriptase purified from AMV or M-MLV (Molony Murine Leukemia Virus) reverse transcriptase purified from *Escherichia coli* expressing a recombinant clone of M-MLV reverse transcriptase, while it is preferred to use AMV reverse transcriptase whose elongation activity and activation temperature are higher than those of M-MLV reverse transcriptase. The reaction temperature can be determined as desired in the context of each enzyme to be used, and for example, 40° C. to 42° C. is preferred. As shown in FIG. 1(*a*), the reaction is initiated after fixing solid-phase primers 2 on surfaces 1*a* of substrates 1 (see FIG. 1(*b*) and (*c*)). Further, FIG. 6 i) shows a liquid-phase chimeric primer hybridized with the 3'-side of the target RNA, and FIG. 6 ii) shows a cDNA strand-RNA strand complex synthesized by a reverse transcription.

Step (e) comprises allowing an RNase that specifically degrades an RNA strand in a DNA strand-RNA strand complex, to act on the cDNA strand-RNA strand complex prepared in step (d) to prepare a single-stranded DNA (−). As for the RNase used in step (e), it is desirable to use an RNase that specifically degrades the RNA strand in the DNA strand-RNA strand complex without suppressing the activity of RNA polymerase. Specifically, RNase H can be exemplified preferably. FIG. 1(*d*) and FIG. 6 iii) show pattern diagrams of the reaction.

Step (f) comprises allowing the single-stranded DNA (−) prepared in step (e) to contact with the solid-phase DNA (+) primer prepared in step (a) in a liquid phase to hybridize the single-stranded DNA (−) and the solid-phase DNA (+) primer, and then extending a DNA (+) strand from the 5' side to 3' side by an enzyme having a DNA-dependent DNA-polymerase activating capacity, using the single-stranded DNA (−) as a template to prepare a double-stranded DNA. Examples include a method wherein an enzyme having a DNA-polymerase activity is reacted in the presence of deoxynucleotides to synthesize a double-stranded cDNA. As for the enzyme having a DNA-polymerase activating capacity, the enzyme needs to have a DNA-dependent DNA-polymerase activating capacity, and preferably, the enzyme is without a deoxyribonuclease (DNase) activity such as 5'- or 3'-exonuclease activity. Further, when an enzyme additionally having a DNA-dependent DNA-polymerase activating capacity, such as the AMV reverse transcriptase, has already been used in the step (d), it is no longer needed to add an enzyme having a DNA-polymerase activating capacity. FIG. 1(*e*) and FIG. 6 iv) show pattern diagrams of the reaction.

Step (g) comprises allowing an RNA polymerase to act on the double-stranded DNA prepared in step (f) to amplify a single-stranded RNA (−), i.e., antisense RNA, by utilizing the RNA-polymerase promoter sequence derived form the DNA (−) strand, hybridizing the 3' side of an amplified single-stranded RNA (−) and a solid-phase DNA (+) primer, and then extending a DNA (+) strand by a reverse transcriptase in the presence of deoxynucleotides to prepare a cDNA strand-RNA strand complex. FIG. 2(*a*) shows a pattern diagram of the reaction wherein single-stranded RNA 9 is synthesized via promoter sequence 8 present on double-stranded cDNA 6 and is then hybridized with solid-phase DNA (+) primer 2. Further, FIGS. 6 iv) and v) show how the antisense RNA is amplified, FIG. 6 vi) shows how the amplified antisense RNA is hybridized with the solid-phase DNA (+) primer, and FIG. 6 vii) shows the cDNA strand-RNA strand complex.

Step (h) comprises allowing an RNase that specifically degrades the RNA strand in a DNA strand-RNA strand complex, to act on the cDNA strand-RNA strand complex prepared in step (g) to prepare a solid-phase single-stranded DNA (+). As the RNase, the above RNase H can be preferably exemplified. FIG. 2(*b*) shows the reaction wherein cDNA strand (+) 10 is synthesized via solid-phase DNA (+) primer 2 to prepare a cDNA strand-RNA strand complex, and then the RNA strand of this cDNA strand-RNA strand complex is degraded to obtain single-stranded cDNA 10. Further, FIG. 6 viii) shows how the RNA strand of the cDNA strand-RNA strand complex is degraded.

Step (i) comprises allowing the solid-phase single-stranded DNA (+) prepared in step (h) to contact with the liquid-phase universal primer prepared in step (b') in a liquid phase to hybridize the single-stranded DNA (+) and the liquid-phase universal primer, and then extending a DNA (−) strand and DNA (+) strand, respectively, from the 5' to the 3' side by an enzyme having a DNA-dependent DNA-polymerase activity to prepare a double-stranded DNA. As the above enzyme, the enzyme used in step (f) can be utilized without change. By increasing the amount of the liquid-phase universal primer in this step (i) to 10 times or more than the number of the liquid-phase chimeric primer in step (d), the amplification reaction is replaced with a reaction which is proceeded solely by the liquid-phase universal primer. This therefore replaces all liquid-phase chimeric primers with universal primers when a simultaneous amplification of plural kinds of genes is intended, and thus achieves a quantitative reaction. FIG. 2(*c*) shows a reaction wherein cDNA strand 10 is hybridized with liquid-phase primer 3*b*, FIG. 6 ix) shows how a single-stranded DNA (+) is hybridized with a labeled liquid-phase universal primer, and FIG. 6 x) shows a labeled double-stranded DNA.

Repeating twice or more the above steps (g) to (i) is preferred for enhancing the quantification accuracy. Since steps (d) to (i) are performed in a single reaction solution as stated above, step (g) to step (i) will be repeated twice or more without a specific operation by adjusting the reaction conditions such as reaction time. FIG. 6 *x*) shows how the single-stranded RNA (−) and the DNA (+) strand of step (g) are amplified following step (i).

Step (j) is a step for quantifying the double-stranded DNAs prepared in step (f) and step (i). The method for detecting or quantifying the synthesized double-stranded DNAs is not particularly limited, and examples include known methods such as a method wherein a labeling reagent for labeling double-stranded DNAs is added in the reaction solution; a method wherein deoxynucleotides are labeled in advance; and a method wherein the primer sequence in a liquid-phase universal primer or liquid-phase chimeric primer is labeled. Further, the fluorescence amount of the fluorescent dye used for quantification can be measured time-dependently by real-time PCR, etc. The measurement values thus obtained can be added up to quantify the obtained DNA-amplification product.

A known labeling reagent can be used as the above labeling reagent for labeling a double-stranded DNA. Examples include a fluorescent dye and coloring reagent, and specific examples include SYBER Green (Takara Bio) which is an intercalator that is inserted into a double-stranded DNA. For example, SYBER Green is inserted by adding SYBER Green in the reaction solution when a double-stranded DNA is formed on a substrate, and thus can achieve a simple labeling. When SYBER Green is used as a labeling reagent, it is preferred to observe the fluorescence over time at 525 nm with the excitation light of 485 nm using a microarray scanner. Further, it is also possible to detect a double-stranded DNA using ethidium bromide which has been inserted into a double-stranded DNA and then making it emit a color by UV radiation.

Examples of a method for labeling deoxynucleotides in advance include a method wherein a fluorescent dye such as FITC, rhodamine, or cyanine including Cy3 or Cy5 is used for labeling, and further, a method wherein biotin, digoxigenin, RI, etc. is used for labeling and a coloring reagent such as alkaline phosphatase or peroxidase is used for a color emission. These labeled deoxynucleotides are used to form a double-stranded DNA on the substrate, and therefore the labeling of the formed double-stranded DNA is achieved in a simple manner. For example, when detecting or quantifying double-stranded DNAs using biotin-labeled dUTP, it is preferred that each enzymatic-reaction solution for biotin-labeling shown in Table 1 and a reagent for a Cy3-labeling reaction shown in Table 2 are used in each reaction solution to perform a reaction at 37° C. for 15 minutes.

TABLE 1

|  |  | Final Concentration |
|---|---|---|
| 10 μM dATP | 8 μL | 1 μM |
| 10 μM dGTP | 8 μL | 1 μM |
| 10 μM dCTP | 8 μL | 1 μM |
| 10 μM Biotin-dUTP | 8 μL | 1 μM |
| 10x Ex Taq Buffer | 8 μL | 1x |
| 10x MPEX BufferA | 8 μL | 1x |
| Deionized Water | 23.2 μL | — |
| Sample DNA | 8 μL | 1/10 |
| TaKaRa Ex Taq | 0.8 μL | — |
| Total | 80 μL |  |

70 μL/chip is needed for the reaction

TABLE 2

|  | For Cy3 Labeling | Final Concentration |
|---|---|---|
| 0.01 μg/μL Streptavidin-Cy3 | 8 μL | 1 ng/μL |
| 1/100 Streptavidin-AP | — | 1/1,000 |
| 10x MPEX BufferA | 8 μL | 1x |
| 2x MPEX BufferB | 40 μL | 1x |
| Deionized Water | 24 μL | — |
| Total | 80 μL |  |

70 μL/chip is needed for the reaction

In the steps (d) to (j), the above-mentioned enzymes, etc. may be added step-wisely, while it is preferred to prepare the reagent needed for all of the steps as a single reaction solution and then introduce it to the substrate. As stated above, the steps (g) to (i) are repeatedly performed to synthesize double-stranded DNAs, and the DNA fragment can be replicated and amplified rapidly and easily without the need of newly adding enzymes such as RNase or DNA polymerase to the reaction system in each repetition. In addition, when introducing a reaction solution to a substrate, the reaction solution is preferably introduced into each concave part by means of surface tension by placing on the substrate a cover that can cover all of the plurality of concave parts provided on the substrate. Further, the use of the cover can not only save the work of dispensing the reaction solution but also prevent contamination and reduce the total amount of the reaction solution, resulting in a cost reduction. Further, the cover is preferably transparent so as to allow an easy detection of the labeling reagent.

The method for detecting or quantifying a target RNA of the present invention allows quantification of double-stranded DNAs formed on a substrate even from trace amounts of sample RNA, and enables a simple quantification of one or more kinds of target RNAs on the same substrate. Further, when detecting or quantifying one or more kinds of pathogenic microorganisms using the method for detecting or quantifying a target RNA of the present invention, culturing is not needed for the detection. This enables a simple and rapid detection of microorganisms, etc. particularly such as those cannot be cultured using a common method. The present method is therefore effective for detecting RNA derived from a pathogenic microorganism, and further, can simply quantify from one sample the RNAs derived from plural kinds of pathogenic microorganisms, because multiplex can be performed simply.

The kit for detecting or quantifying RNA of the present invention is not particularly limited as long as it is a kit comprising: a solid-phase DNA (+) primer wherein the 5' end of the primer comprising a 5'-side target specific sequence of the target RNA is fixed on the surface of a substrate; a liquid-phase cDNA (−) primer wherein an RNA-polymerase promoter sequence is added to the 5'-end side of the primer comprising a cDNA sequence which is complementary to the 3'-side sequence of the target RNA; a reverse transcriptase; an RNA polymerase; and an RNase that specifically degrades the RNA strand in a DNA strand-RNA strand complex. The liquid-phase cDNA (−) primer is preferably a liquid-phase chimeric primer wherein an RNA-polymerase promoter sequence is added via a tag sequence to the 5'-end side of the primer comprising a cDNA sequence which is complementary to the 3'-side sequence of the target RNA. Further, a preferred kit comprises a liquid-phase universal primer wherein an RNA-polymerase promoter sequence is added to the 5' end of the tag sequence. The preferred kit further comprises as the primer sequence a labeled promoter sequence such as a biotinylated promoter sequence, and a labeling reagent such as a fluorescent dye. Further, a DNA-dependent DNA polymerase can also be contained. By using the kit for detecting or quantifying RNA of the present invention, a target RNA such as a bacteria-specific RNA strand in 16S rRNA can be detected or quantified simply and rapidly.

The present invention will be described more specifically with reference to the following examples, while the scope of the present invention will not be limited to these examples.

Reference Example 1

Quantitative Detection of Target RNA Using Liquid-Phase Universal Primer

NASBA method was performed to investigate if it can quantify RNA having a target RNA sequence. RNA extracted from *H. influenzae* was used as the target RNA and a poly-T sequence consisting of 20 base pairs was used as a negative control. Further, as for primers for the target RNA, DNA having a nucleotide sequence homologous to the nucleotide sequence at positions 165 to 187 of 16S rRNA gene of *H. influenzae* was used as a forward primer. Further, as a reverse primer, DNA having a nucleotide sequence complementary to the nucleotide sequence at positions 502 to 519 of 16S rRNA gene, wherein a tag sequence consisting of 13 nucleotides (AGAAGGAGCAGGA) is added to its 5' side and a promoter sequence is further added to the 5' side of the tag sequence was used. As the promoter sequence, the promoter sequence (5'-TAATACGACTCACTATAGGGCGA-3') of T7RNA polymerase was used. As a universal primer, DNA wherein a promoter sequence of T7RNA polymerase is added to the 5' side of the tag sequence, consisting of 13 nucleotides (AGAAGGAGCAGGA) was used.

Figure 3:
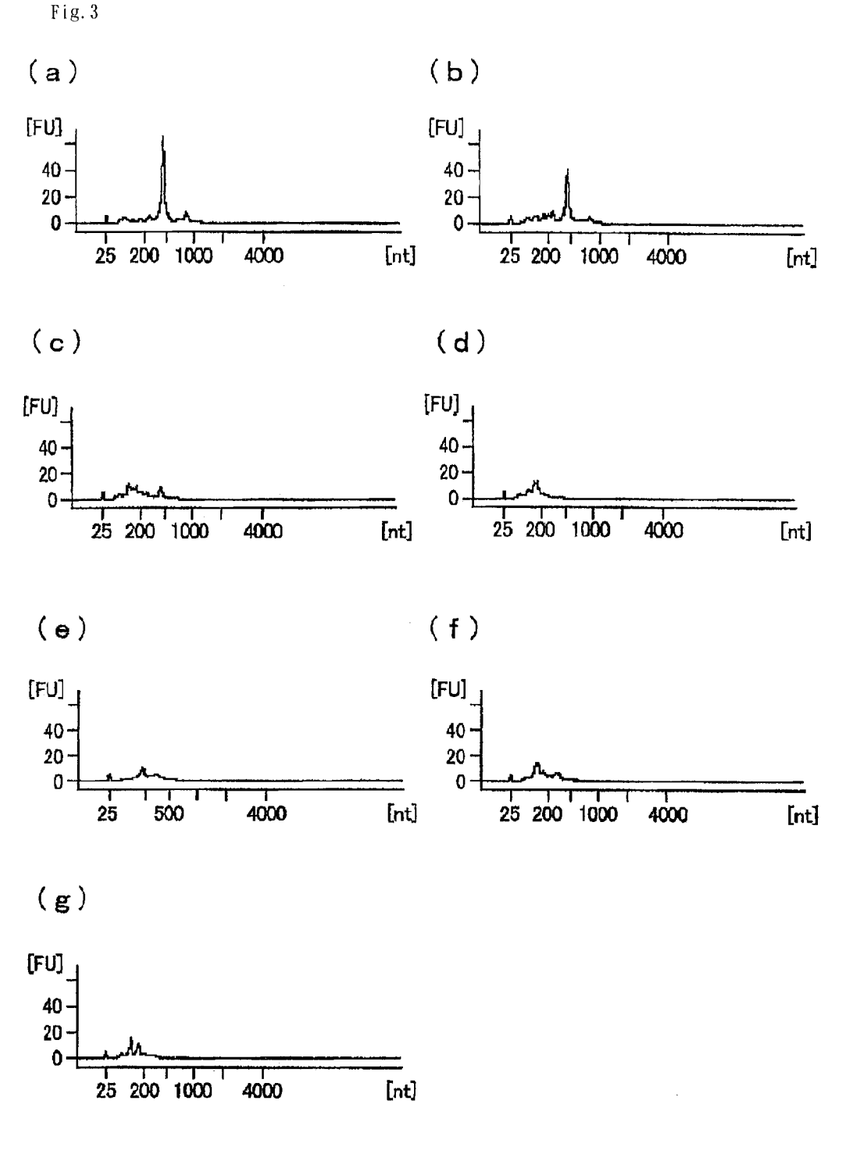
FIG. 3 This figure shows quantitative detections of amplified products (RNAs).

First, the tube surface was coated with polymer having active ester, and thereby the surface was conferred a binding activity to the amino group introduced to the 5' end of the forward primer which was used as a solid-phase primer. Next, extracted RNA of *H. influenzae* was suspended in a buffer solution (50 mM Tris-HCl, pH 8.3, 6 mM MgCl2, and 40 mM KCl), so as to prepare solutions containing $10^4$, $10^5$, $10^6$, $10^7$, $10^8$, and $10^9$ copies of the RNA, respectively. 0.05 µM liquid-phase chimeric primer of the present invention, 2 µM liquid-phase universal primer of the present invention, and 1000 pg of SYBER Green (Takara) were mixed with 10 µl of Master Mix (Biomerieux) for exclusive use as a NASBA reagent. The resultant mixture was heated at 95° C. for 30 seconds, and then allowed to stand still at 65° C. for 5 minutes to prepare an extracted-RNA solution. Subsequently, 10 mM DTT and 5 µl of an enzyme mixture (Biomerieux) of 40 units of AMV reverse transcriptase, 0.4 unit of RNase H, and 20 units of T7RNA polymerase were added to the extracted-RNA solution so that the final volume of the reaction solution becomes 20 µl. Then, each tube was placed in a constant temperature bath set at 41° C. to amplify the RNA by NASBA method. Next, the amplified products (RNA) were electrophoresed to confirm whether the RNAs of *H. influenzae* were amplified quantitatively by the NASBA method, and the results are shown in FIG. 3. In FIG. 3, the horizontal axis represents the number of nucleotides and the vertical axis represents the fluorescence intensity. It is observed from FIG. 3 that the fluorescence intensity of the RNA amplification products (368 nt) increased as the copy number of genome served as a template increased. This confirmed that the target RNA was amplified quantitatively.

Reference Example 2

Optimal Fixing Amount of Solid-Phase DNA (+) Primer

Figure 4:
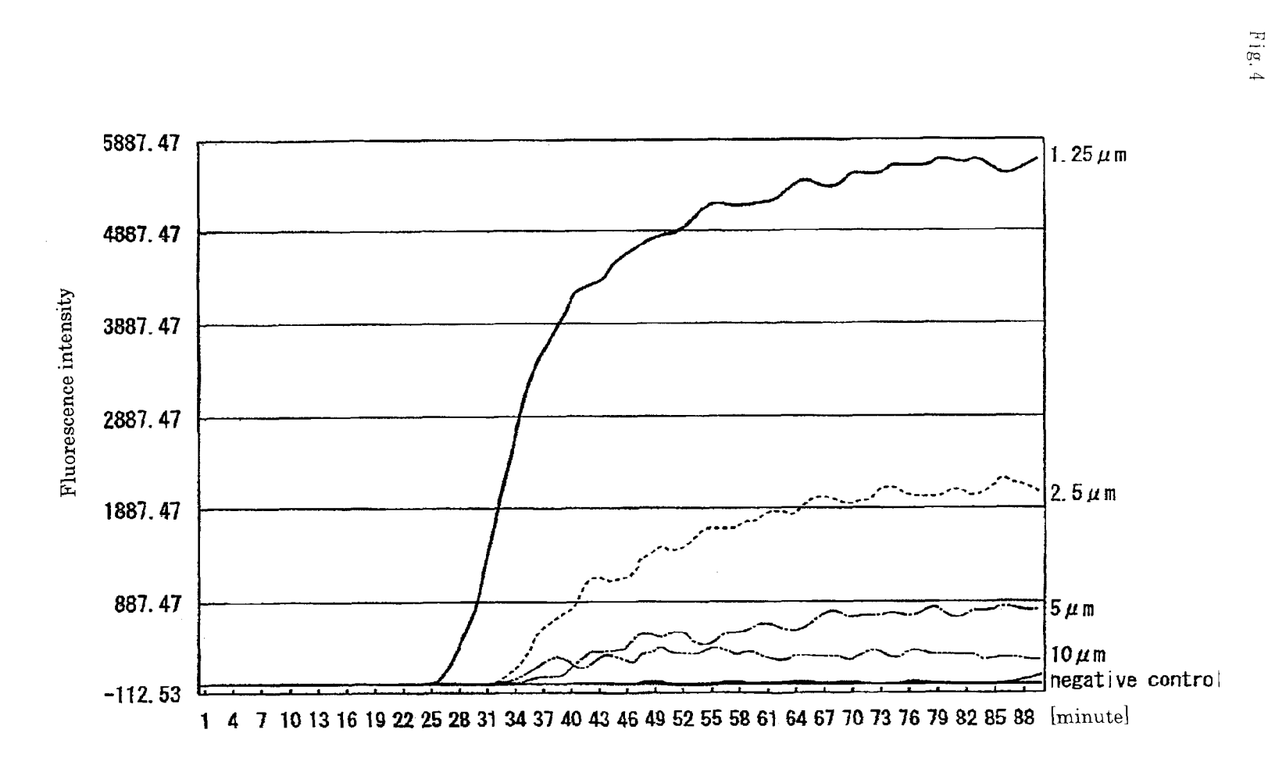
FIG. 4 This figure shows a time-dependent detection of amplified DNA so as to determine the optimal amount of a primer. The horizontal axis represents time and the vertical axis represents fluorescence intensity.

Next, to investigate the amount to be fixed of solid-phase DNA (+) primer, solid-phase primer corresponding to *H. influenzae* was dissolved in an amount of 1.25 W, 2.5 µl, 5 W, and 10 µM in a spotting solution for fixing (Sumitomo Bakelite), and 1 µl of each mixture was added dropwise into each tube. After the dropping, each tube was kept warm at 80° C. for 1 hour, to provide tubes for detection. Then, a reaction solution was prepared using $10^8$-copy extracted RNA of *H. influenzae* and the above tubes for detection, which was followed by RNA amplification by NASBA method. Further, a poly-T sequence consisting of 20 base pairs was used as a negative control. During the RNA amplification, amplified DNAs were detected over time by measuring the fluorescence at 525 nm by the excitation light of 485 nm each minute for 60 minutes to determine the optimal amount of the primer. The results are shown in FIG. 4. In FIG. 4, the horizontal axis represents time and the vertical axis represents the fluorescence intensity. It is observed from FIG. 4 that the amplification of the target nucleic acids was most efficient when the amount of the primer fixed on the tube was 1.25 µM.

Example 1

Quantitative Detection of Target RNA

Figure 5:
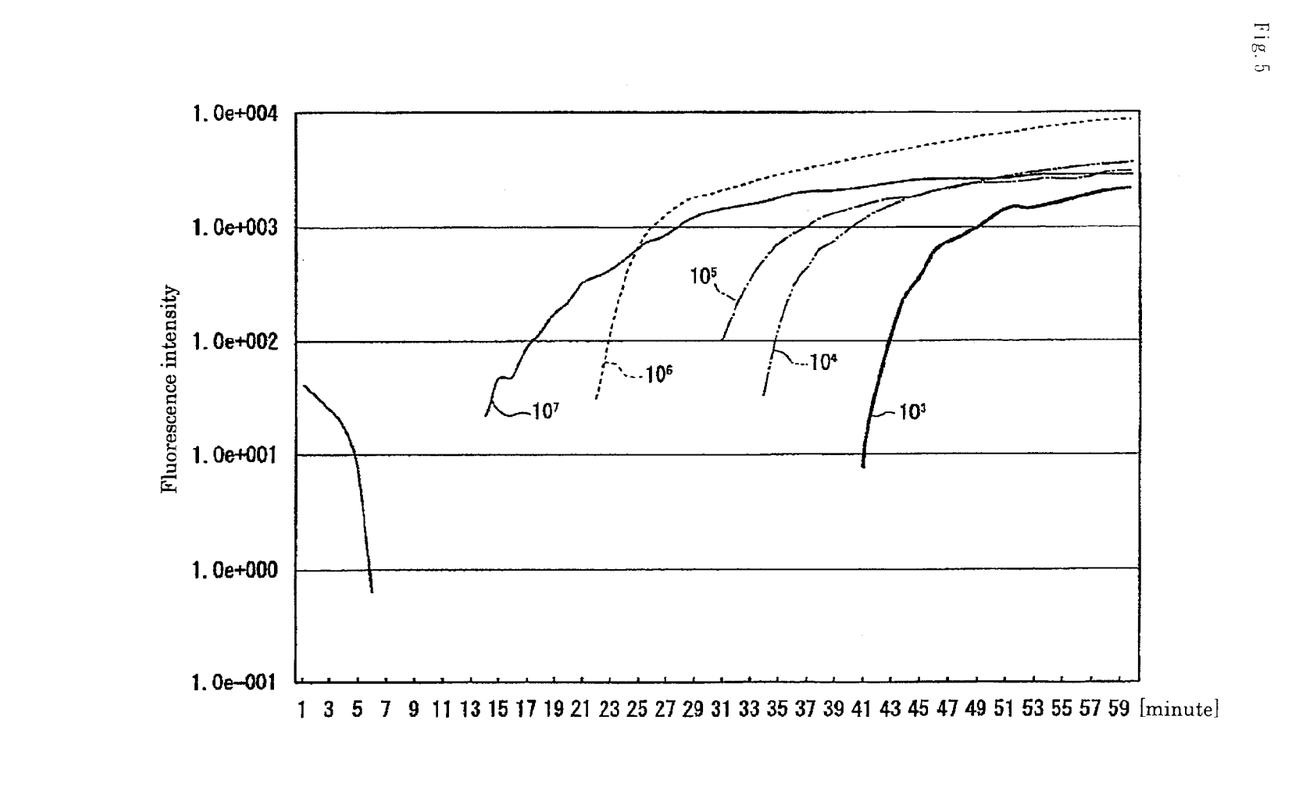
FIG. 5 This figure shows a quantitative and time-dependent detection of the nucleic-acid amplification product (DNA).

Next, sample RNA solutions were prepared in the same manner as Reference Example 1 so that the solutions contain $10^3$, $10^4$, $10^5$, $10^6$ and $10^7$ copies of extracted nucleic acids (RNA) of *H. influenzae*. The RNA-extract solution was added to each tube to which 1.25 µl solid-phase DNA (+) primer had been bound, and the nucleic acids were amplified by NASBA method in the same manner as Reference Example 1. Further, a poly-T sequence consisting of 20 base pairs was used as a negative control. During the nucleic-acid amplification, the amplified DNAs were detected over time by measuring the fluorescence at 525 nm by the excitation light of 485 nm each minute for 60 minutes. The results are shown in FIG. 5. In FIG. 5, the vertical axis of the graph represents fluorescence intensity and the horizontal axis represents the reaction time. According to FIG. 5, the total amount of the nucleic acid amplification product (DNA) by NASBA method is represented by the integral value of each curve. It was observed that the amount of nucleic-acid amplification product increased as the copy number of extracted RNA increased. This provided the observation that RNA having a target specific sequence was successfully quantified with the tube to which a solid-phase DNA (+) primer had been fixed.

Example 2

Detection or Quantification of Plural Kinds of Pathogenic Bacteria

The method for detecting or quantifying a target RNA of the present invention is used to detect or quantify causative bacteria of pneumonia, for a patient who is possibly affected by pneumonia.

(Preparation of Solid-Phase Primer)

The nucleotide sequence (#1) shown by SEQ ID NO: 1 of the sequence listing which is specific to *Streptococcus pneumoniae*, the nucleotide sequence (#2) shown by SEQ ID NO: 2 which is specific to *Hemophilus influenzae*, the nucleotide sequence (#3) shown by SEQ ID NO: 3 which is specific to *Mycoplasma pneumoniae*, the nucleotide sequence (#4) shown by SEQ ID NO: 4 which is specific to *Chlamydia pneumoniae*, the nucleotide sequence (#5) shown by SEQ ID NO: 5 which is specific to *Legionella* spp., the nucleotide sequence (#6) shown by SEQ ID NO: 6 which is specific to *Klebsiella pneumoniae*, the nucleotide sequence (#7) shown by SEQ ID NO: 7 which is specific to *Pseudomonas aereruginosae*, and the nucleotide sequence (#8) shown by SEQ ID NO: 8 which is specific to *Moraxella catarrahalis* were used as primers having a DNA sequence corresponding to the 5'-side target specific sequence of the target RNA, and then the primers wherein an amino group was introduced to their 5' end were prepared by a standard method and used for the preparation of solid-phase DNA (+) primers. A 96-well multiplate was used as a substrate and each of the above 8 kinds of primers was dissolved in a spotting solution for fixing to prepare a 0.5 µM-concentration DNA-primer solution. Each primer was allocated 12 wells and each primer solution was added dropwise into 12 wells and then kept warm at 80° C. for 1 hour to fix each of the 8 kinds of primers onto 12 wells, respectively, to serve as #1 to #8 multiplex solid-phase DNA (+) primers.

(Preparation of Liquid-Phase Chimeric Primer)

Liquid-phase chimeric primers were prepared using as the 3'-side sequence of the target RNA the nucleotide sequence shown by SEQ ID NO: 9 of the sequence listing, which is specific to bacteria such as *Streptococcus pneumoniae, Hemophilus influenzae, Legionella* spp., *Klebsiella pneumoniae, Pseudomonas aereruginosae*, and *Moraxella catarrahalis* and the nucleotide sequence shown by SEQ ID NO: 10 of the sequence listing, which is specific to bacteria such as *Mycoplasma pneumoniae* and *Chlamydia pneumoniae*. Then, the tag sequence shown by SEQ ID NO: 14 was added to the 5' end of the primers comprising a cDNA sequence complementary to the above sequences. By further adding a biotin-labeled promoter sequence of T7 polymerase shown by SEQ ID NO: 11 to the 5' end of the tag sequence, a liquid-phase chimeric primer was prepared.

(Preparation of Liquid-Phase Universal Primer)

A liquid-phase universal primer was prepared by adding a biotin-labeled promoter sequence of T7 polymerase shown by SEQ ID NO: 11 to the 5' end of the tag sequence shown by SEQ ID NO: 14.

Next, an RNA extraction solution of *Hemophilus influenzae*, *Mycoplasma pneumoniae* and *Moraxella catarrahalis* was suspended in a buffer (50 mM Tris-HCl, pH 8.3, 6 mM MgCl2, and 40 mM KCl), so as to prepare solutions containing $10^4$, $10^5$, $10^6$, $10^7$, $10^8$, and $10^9$ copies of the RNAs, respectively. 0.05 μM liquid-phase chimeric primer and 2 μM liquid-phase universal primer were mixed with 10 μl of Master Mix (Biomerieux) which was for exclusive use as a NASBA reagent. The resultant mixture is heated at 95° C. for 30 seconds, and then allowed to stand still at 65° C. for 5 minutes. Then, 10 mM DTT and 5 μl of an enzyme mixture (Biomerieux) of 40 units of AMV reverse transcriptase, 0.4 unit of RNase H, and 20 units of T7RNA polymerase were added to the extracted-RNA solution to prepare the reaction solution with the final volume of 20 μl. Subsequently, the substrate was placed in a constant temperature bath set at 41° C. to allow the reaction to proceed. From the initiation of the reaction, each reaction was sequentially stopped each minute over 12 minutes, and for each of #1 to #8 solutions that completed the reaction, a coloring reaction was performed using streptavidin-alkaline phosphatase as a biotin substrate, and 5-bromo-4-chloro-3-indole-phosphoric acid and 4-nitro blue tetrazolium chloride as chromogenic substances, to observe blue color.

The invention claimed is:

1. A method for detecting or quantifying a target RNA, comprising the following steps (a) to (j):
   (a) a step of fixing a 5' end of a primer comprising a DNA sequence corresponding to a 5'-side target specific sequence of the target RNA on a surface of a substrate to prepare a solid-phase DNA (+) primer;
   (b) a step of preparing a liquid-phase cDNA (−) primer wherein an RNA-polymerase promoter sequence is added via a tag sequence to a 5'-end side of a primer comprising a cDNA sequence which is complementary to a 3'-side sequence of the target RNA, and a liquid-phase universal primer wherein an RNA-polymerase promoter sequence is added to a 5' end of a tag sequence;
   (c) a step of preparing a sample RNA comprising a 3'-side sequence and 5'-side target specific sequence of the target RNA;
   (d) a step of allowing the liquid-phase cDNA (−) primer prepared in step (b) to contact with the sample RNA strand prepared in step (c) in a liquid phase to hybridize the liquid-phase cDNA (−) primer and the sample RNA, and then extending a DNA (−) strand by a reverse transcriptase to prepare a cDNA strand-RNA strand complex;
   (e) a step of allowing an RNase that specifically degrades an RNA strand in a DNA strand-RNA strand complex, to act on the cDNA strand-RNA strand complex prepared in step (d) to prepare a single-stranded DNA (−);
   (f) a step of allowing the single-stranded DNA (−) prepared in step (e) to contact in a liquid phase, with the solid-phase DNA (+) primer prepared in step (a) to hybridize the single-stranded DNA (−) and the solid-phase DNA (+) primer, and then extending a DNA (+) strand by an enzyme having a DNA-dependent DNA-polymerase activity to prepare a double-stranded DNA;
   (g) a step of allowing an RNA polymerase to act on the double-stranded DNA prepared in step (f) to amplify a single-stranded RNA (−) utilizing an RNA-polymerase promoter sequence derived from the DNA (−) strand, hybridizing an amplified single-stranded RNA (−) and a solid-phase DNA (+) primer, and then extending a DNA (+) strand by a reverse transcriptase to prepare a cDNA strand-RNA strand complex;
   (h) a step of allowing an RNase that specifically degrades an RNA strand in a DNA strand-RNA strand complex, to act on the cDNA strand-RNA strand complex prepared in step (g) to prepare a solid-phase single-stranded DNA (+);
   (i) a step of allowing the solid-phase single-stranded DNA (+) prepared in step (h) to contact with the liquid-phase universal primer prepared in step (b) in a liquid phase to hybridize the single-stranded DNA (+) and the liquid-phase universal primer, and then extending a DNA (−) strand by an enzyme having a DNA-dependent DNA-polymerase activity to prepare a double-stranded DNA; and
   (j) a step of quantifying the double-stranded DNAs prepared in step (f) and step (i).

2. The detection or quantification method according to claim 1, wherein step (g) to step (i) are repeated twice or more.

3. The detection or quantification method according to claim 1 or 2, wherein step (d) to step (j) are performed in a single reaction solution.

4. The detection or quantification method according to claim 1 or 2, wherein a plurality of target RNAs are detected or quantified on a same substrate.

5. The detection or quantification method according to claim 1 or 2, wherein the tag sequence is sequence AGAAGG, or AGAAGG to which any 7 nucleotides rich in AG are further added.

6. The detection or quantification method according to claim 1 or 2, wherein the tag sequence is AGAAGGAGCAGGA.

7. The detection or quantification method according to claim 1 or 2, wherein a liquid-phase universal primer concentration is 10 times or more than a liquid-phase cDNA (−) primer concentration.

8. The detection or quantification method according to claim 1 or 2, wherein a liquid-phase universal primer in which the RNA-polymerase promoter sequence is a labeled promoter sequence, is used.

9. The detection or quantification method according to claim 8, wherein the labeled promoter sequence is a biotinylated promoter sequence.

10. The detection or quantification method according to claim 1 or 2, wherein step (i) is performed in the presence of a labeling reagent.

11. The detection or quantification method according to claim 10, wherein the labeling reagent is a fluorescent dye.

12. The detection or quantification method according to claim 1 or 2, wherein the reverse transcriptase is used as an enzyme having a DNA-dependent DNA-polymerase activity.

13. The detection or quantification method according to claim 1 or 2, wherein the target RNA is a bacteria-specific RNA strand in 16S rRNA.

14. A method for detecting or quantifying one or more pathogenic microorganisms using the method for detecting or quantifying RNA according to claim 1 or 2.

15. A kit for detecting or quantifying RNA, comprising a solid-phase DNA (+) primer wherein a 5' end of the primer comprising a 5'-side target specific sequence of a target RNA is fixed on a surface of a substrate; a liquid-phase cDNA (−) primer wherein an RNA-polymerase promoter sequence is added via a tag sequence to a 5'-end side of the primer comprising a cDNA sequence which is complementary to a 3'-side sequence of the target RNA, wherein the tag sequence is sequence AGAAGG, or AGAAGG to which any 7 nucleotides rich in AG are further added; a liquid-phase universal primer wherein an RNA-polymerase promoter sequence is added to a 5'-end side of the tag sequence; a reverse transcriptase; an RNA polymerase; and an RNase that specifically degrades an RNA strand in a DNA strand-RNA strand complex.

16. The kit for detecting or quantifying RNA according to claim 15, wherein the tag sequence is AGAAGGAGCAGGA.

17. The kit for detecting or quantifying RNA according to claim 15 or 16, wherein the RNA-polymerase promoter sequence is a labeled promoter sequence.

18. The kit for detecting or quantifying RNA according to claim 17, wherein the labeled promoter sequence is a biotinylated promoter sequence.

19. The kit for detecting or quantifying RNA according to claim 15 or 16, further comprising a labeling reagent.

20. The kit for detecting or quantifying RNA according to claim 19, wherein the labeling reagent is a fluorescent dye.

21. The kit for detecting or quantifying RNA according to claim 15 or 16, further comprising a DNA-dependent DNA polymerase.

22. The kit for detecting or quantifying RNA according to claim 15 or 16, wherein the target RNA is a bacteria-specific RNA strand in 16S rRNA.

* * * * *